US012605239B2

(12) United States Patent
Beckstead et al.

(10) Patent No.: US 12,605,239 B2
(45) Date of Patent: Apr. 21, 2026

(54) ENHANCEMENT OF HYDRATION AND IMPROVEMENT IN GUT HEALTH THROUGH CLOACAL DELIVERY OF PRODUCTS

(71) Applicant: North Carolina State University, Raleigh, NC (US)

(72) Inventors: Robert Byron Beckstead, Raleigh, NC (US); Peter R. Ferket, Raleigh, NC (US); Olivia Ann Wedegaertner, Raleigh, NC (US); Raveendra Rangarao Kulkarni, Cary, NC (US)

(73) Assignee: North Carolina State University, Raleigh, NC (US)

( * ) Notice: Subject to any disclaimer, the term of this patent is extended or adjusted under 35 U.S.C. 154(b) by 1167 days.

(21) Appl. No.: 17/389,026

(22) Filed: Jul. 29, 2021

(65) Prior Publication Data

US 2022/0031440 A1 Feb. 3, 2022

Related U.S. Application Data

(60) Provisional application No. 63/058,299, filed on Jul. 29, 2020.

(51) Int. Cl.
*A61D 7/00* (2006.01)
*A61K 9/00* (2006.01)
*A61K 35/741* (2015.01)

(52) U.S. Cl.
CPC .............. *A61D 7/00* (2013.01); *A61K 9/0031* (2013.01); *A61K 35/741* (2013.01)

(58) Field of Classification Search
CPC ....... A61D 7/00; A61K 9/0031; A61K 35/741
See application file for complete search history.

(56) References Cited

U.S. PATENT DOCUMENTS

| | | |
|---|---|---|
| 2,910,407 A | 10/1959 | Hitchner |
| 5,028,440 A | 7/1991 | Nissen |
| 5,308,615 A | 5/1994 | DeLoach |
| 7,037,501 B2 | 5/2006 | El Halawani |
| 8,431,138 B2 | 4/2013 | Agin |
| 8,465,755 B2 | 6/2013 | Curtiss, III |
| 9,393,275 B2 | 7/2016 | Wolfenden |
| 9,580,718 B2 | 2/2017 | Curtiss, III |
| 9,878,036 B2 | 1/2018 | Coulter |
| 9,884,099 B2 | 2/2018 | Barta |
| 10,022,435 B2 | 7/2018 | Ciaramella |
| 10,258,688 B2 | 4/2019 | Hargis |
| 10,456,459 B2 | 10/2019 | Dominowski |
| 10,624,366 B2 | 4/2020 | Embree |
| 2018/0333443 A1* | 11/2018 | Embree ................. C12N 1/205 |

OTHER PUBLICATIONS

Felfoldi et al., "In ovo vitelline duct ligation results in transient changes of bursal microenvironments." Immunology, 116: 267-275. (Year: 2005).*

Hemmi, H., et al., "A Toll-like Receptor Recognizes Bacterial Dna," Nature, vol. 408, 2000, pp. 740-745.

Ahmad-Nejad, P., et al., "Bacterial CpG-DNA and Lipopolysaccharides Activate Toll-like Receptors at Distinct Cellular Compartment," European Journal of Immunology, vol. 32, 2002, pp. 1958-1968.

Dalloul, A.R., et al., "In ovo Administration of CpG Oligodeoxynucleotides and the Recombinant Microneme Protein MIC2 Protects Against Eimeria Infections," Vaccine, vol. 23, 2005, pp. 3108-3113.

Sercombe L., et al., "Advances and Challenges of Liposome Assisted Drug Delivery," Frontiers in Pharmacology, vol. 06, Article No. 286, Dec. 1, 2015, pp. 1-13.

Zare, H., et al., "Carbon Nanotubes: Smart Drug/Gene Delivery Carriers," International Journal of Nanomedicine, vol. 16, 2021, pp. 1681-1706.

Renu, S., et al., "Chitosan Nanoparticle Based Mucosal Vaccines Delivered Against Infectious Diseases of Poultry and Pigs," Frontiers in Bioengineering and Biotechnology, vol. 08, Article No. 558349, Nov. 13, 2020, 16 Pages.

Muir, W.I., et al., "Immunity, Vaccination and the Avian Intestinal Tract," Developmental and comparative immunology, vol. 24, No. 2-3, Mar.-Apr. 2000, pp. 325-342.

Jin, Z., et al., "Adjuvants and Delivery Systems Based on Polymeric Nanoparticles for Mucosal Vaccines," International Journal of Pharmaceutics, vol. 572, Dec. 15, 2019, 58 Pages.

Silva, S.Q., et al., "Microbial dynamics during azo dye degradation in a UASB reactor supplied with yeast extract," Brazilian Journal of Microbiology, vol. 45, No. 4, pp. 1153-1160 (2014).

Yurina, V., "Live Bacterial Vectors—A Promising DNA Vaccine Delivery System," Medical Sciences, vol. 06, No. 02, Article No. 27, 2018, 12 Pages.

Wilson, H.L., et al., "Mucosal Vaccine Development for Veterinary and Aquatic Diseases," Mucosal Vaccines, 2020, pp. 811-829.

* cited by examiner

Primary Examiner — Suzanne M Noakes
Assistant Examiner — Ciara A McKnight
(74) Attorney, Agent, or Firm — Jenkins, Taylor & Hunt, P.A.

(57) ABSTRACT

In some embodiments, the presently disclosed subject matter provides a method of delivering a bioactive composition to ceca of a bird. In some embodiments, the method comprises (a) providing a bioactive composition; (b) delivering a treatment effective amount of the bioactive composition to a cloaca of the bird; and (c) providing stimulation to a vent of the bird; whereby delivery of the bioactive composition to the ceca of the bird is accomplished.

14 Claims, 7 Drawing Sheets
(7 of 7 Drawing Sheet(s) Filed in Color)

1mL dye given cloacally, held for 1 minute

Turkey, 3wk old

After defecating, blue dye only visible in fecal matter, not in ceca.

1mL dye given cloacally, held for 5 minutes

Turkey, 3wk old

After defecating, blue dye visible in the top half of the cecal tonsils (in the colon and about ½ inch into the ceca)

ENHANCEMENT OF HYDRATION AND IMPROVEMENT IN GUT HEALTH THROUGH CLOACAL DELIVERY OF PRODUCTS

RELATED APPLICATIONS

The presently disclosed subject matter claims the benefit of U.S. Provisional Patent Application Ser. No. 63/058,299, filed Jul. 29, 2020, the disclosure of which is incorporated herein by reference in its entirety.

TECHNICAL FIELD

The presently disclosed subject matter relates in some embodiments to methods of enhancing hydration, improving gut health, and otherwise affecting a subject through cloacal delivery of products.

BACKGROUND

Poultry production is an important part of the agricultural economy in the United States with a total economic activity of $495.1 billion. Early chick/poult mortality associated with dehydration is often a result of conditions associated with hatching birds, length of transportation to growing units, and early environmental stressors. In many cases, birds that arrive at their point of placement at the farm are dehydrated and hypoglycemic. This condition weakens the animals making them unable to find and consume water, thereby exacerbating the condition which can lead to mortality or stunted growth. Mortality due to dehydration and hypoglycemia is both an economic and welfare issue for poultry production companies, especially poultry breeding companies who must air-transport their high-value stock to far international destinations. Thus, methods of enhancing hydration, improving gut health, and/or otherwise affecting a subject represent a need in the art.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, the presently disclosed subject matter provides a method of delivering a bioactive composition to ceca of a bird. In some embodiments, the method comprises (a) providing a bioactive composition; (b) delivering a treatment effective amount of the bioactive composition to a cloaca of the bird; and (c) providing stimulation to a vent of the bird; whereby delivery of the bioactive composition to the ceca of the bird is accomplished.

In some embodiments, the bioactive composition is water or comprises a water-based solution or suspension. In some embodiments, the bioactive composition comprises a component selected from the group comprising a prebiotic, a probiotic, a nutrient, an enteric modulator, an osmolyte, a vaccine, fiber, water, and any combination thereof.

In some embodiments, the bioactive composition contains from about one-half to about one hundred calories. In some embodiments, the bioactive composition has an osmotic pressure not greater than 800 milliosmoles. In some embodiments, the treatment effective amount ranges from about 0.5 to about 7.5 mL of bioactive composition solution per kg of live weight of subject. In some embodiments, the treatment effective amount ranges from about 0.01 to about 0.06 mL per gram of live body weight.

In some embodiments, the treatment effective amount comprises bacteria ranging from about $1 \times 10^5$ colony forming units (cfu) to about $8 \times 10^9$ cfu. In some embodiments, the bioactive composition comprises a probiotic component and a vaccine component. In some embodiments, the bioactive composition comprises two or more components present in a synergistically effective amount.

In some embodiments, delivering a treatment effective amount of the bioactive composition to a cloaca of the bird comprises inserting a delivery device into the cloaca for a distance sufficient to provide delivery of the bioactive composition to the ceca. In some embodiments, the distance sufficient to provide for delivery of the bioactive composition to the ceca comprises about 0.25 to about 3 centimeters (cm). In some embodiments, the delivery device comprises a pipette or other blunt tubular device.

In some embodiments, the bird is selected from the group comprising chickens, turkeys, ducks, geese, quail, pheasant, and ostrich. In some embodiments, the bird is treated prior to, during, and/or after transport. In some embodiments, the method comprises repeating steps (b) and (c) one or more times.

In some embodiments, the presently disclosed subject matter provides a bioactive composition adapted for cloacal administration to a bird in need of receiving treatment by the bioactive composition. In some embodiments, the bioactive composition comprises two or more components selected from the group comprising a prebiotic, a probiotic, a nutrient, an enteric modulator, an osmolyte, a vaccine, fiber, water, and any combination thereof, wherein at least one of the two or more components is present in a treatment effective amount.

In some embodiments, the bioactive composition is water or comprises a water-based solution or suspension. In some embodiments, the bioactive composition comprises a component selected from the group comprising a prebiotic, a probiotic, a nutrient, an enteric modulator, an osmolyte, a vaccine, fiber, water, and any combination thereof.

In some embodiments, the bioactive composition contains from about one-half to about one hundred calories. In some embodiments, the bioactive composition has an osmotic pressure not greater than 800 milliosmoles. In some embodiments, the treatment effective amount ranges from about 0.5 to about 7.5 mL of bioactive composition solution per kg of live weight of subject. In some embodiments, the treatment effective amount ranges from about 0.01 to about 0.06 mL per gram of live body weight.

In some embodiments, the treatment effective amount comprises bacteria ranging from about $1 \times 10^5$ colony forming units (cfu) to about $8 \times 10^9$ cfu. In some embodiments, the bioactive composition comprises a probiotic component and a vaccine component. In some embodiments, the bioactive composition comprises two or more components present in a synergistically effective amount.

Accordingly, an object of the presently disclosed subject matter is to provide a method of enhancing hydration, improving gut health, and/or otherwise affecting a subject through cloacal delivery of products, including in both food animals and non-food animals such as companion animals, zoo animals, and endangered species.

An object of the presently disclosed subject matter having been stated hereinabove, and which is achieved in whole or in part by the compositions and methods disclosed herein, other objects will become evident as the description proceeds when taken in connection with the accompanying Figures and EXAMPLES as best described herein below.

BRIEF DESCRIPTION OF THE FIGURES

The patent or application file contains at least one drawing executed in color. Copies of this patent or patent application publication with color drawing(s) will be provided by the Office upon request and payment of the necessary fee.

Reference will now be made to the accompanying drawings, which are not necessarily drawn to scale.

DETAILED DESCRIPTION

Figure 1:
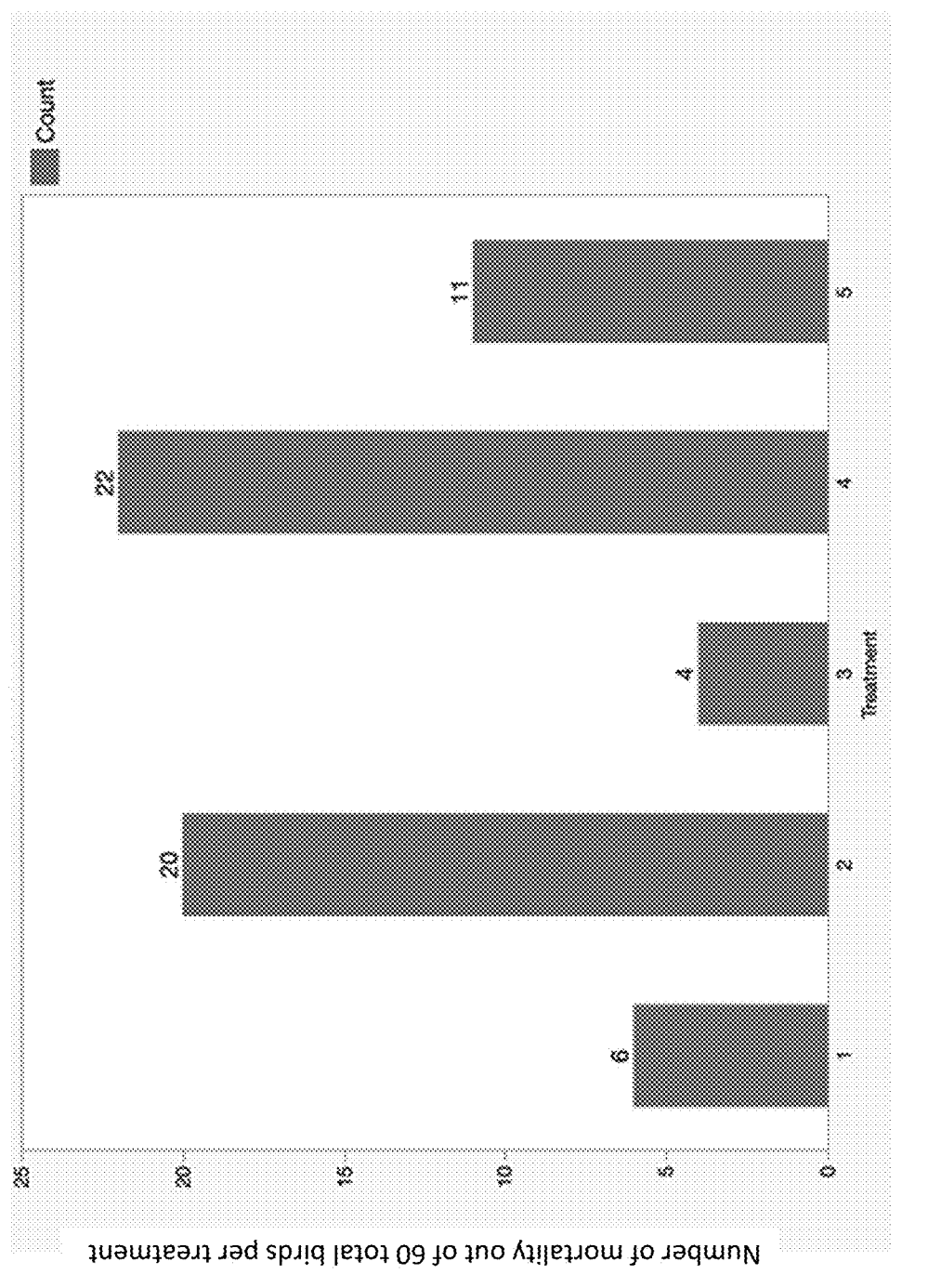
FIG. 1 is a histogram of the mortalities by treatment for EXAMPLE 4 below. The y-axis is the number of mortality out of 60 total birds per treatment and the x-axis is the treatment administered as described in EXAMPLE 4.

Poultry production is an important part of the agricultural economy in the United States with a total economic activity of $495.1 billion. Early chick and poult (young turkey) mortality associated with dehydration is often a result of conditions associated with hatching birds, length of transportation to growing units and early environmental stressors. In some cases, birds arrive at their point of placement at the farm dehydrated and hypoglycemic which weakens the birds, making them unable to find and consume water. This exacerbates the condition which can eventually lead to stunted growth or mortality. Mortality due to dehydration and hypoglycemia is both an economic and welfare issue for poultry production companies, especially poultry breeding companies who must air-transport their high-value stock to far international destinations. Early poultry nutrition and hydration is critical for the utilization of the yolk sac and development of a healthy gastrointestinal tract (GIT), including the establishment of the enteric microbiome which makes the bird more resistant to disease. Effective delivery of prebiotics (e.g., mannan-oligosaccharides, fructo-oligosaccharides, galacto-oligosaccharides, xylo-oligosaccharides, and cellulose), probiotics (e.g., commensal bacterial inoculates, direct-fed microbials, *Lactobacillus* sp, *Streptococcus* sp., *C. butyricum, Bacillus* sp.), nutrients (e.g., trace minerals, vitamins, organic acids, volatile fatty acids, and amino acids), osmolytes (e.g. betaine), vaccines (e.g. *cocci, salmonella*), and water to the chick or poult can prevent early mortality and improve production parameters.

The digestive tract of almost every animal moves food through it using a muscular wave-like movement called peristalsis. Poultry also have the unique ability of reverse-peristalsis, meaning digesta can move backwards in the GIT from the cloaca and colon to the ceca and ileum, from the ileum to the jejunum, from the jejunum to the duodenum, and from the duodenum into the gizzard-proventriculus. At the junction of the colon and the distal ileum are two blind pouches, called ceca. The ceca are reservoirs for intestinal microbes and are also a major site, like the ileum and colon, for water reabsorption. What makes the ceca unique from the rest of the GIT is that digesta is held in the cecal pouches for approximately 6-12 hours while microbial fermentation occurs. Reverse-peristalsis gives birds the ability to pick up bacteria, protozoa, parasites, and fine particles from the litter and transport them backwards from the cloaca to the ceca where they can grow and cause serious spread of disease. In accordance with aspects of the presently disclosed subject matter, this unique behavior is utilized to deliver any liquid suspension of nutrients, prebiotics, probiotics and/or vaccines directly to the ceca of birds.

Aspects of the presently disclosed subject matter include but are not limited to the following:

Delivery of water through the cloaca to the ceca and colon to enhance hydration before transport or rehydration after transport.

Addition of signaling molecules (short-chain volatile fatty acids, such as acetate, butyrate, lactate; osmolytes, such as trimethylglycine, arginine, glutamine) to the water to stimulate water uptake.

Delivery of certain probiotics, prebiotics, and/or cecal microbial inoculants directly to the ceca to allow for the colonization of commensal bacteria in the ceca.

Delivery of certain probiotics, prebiotics, and/or cecal microbial inoculants directly to the ceca to discourage the colonization of enteric pathogens that compete for nutrients in the ceca.

Delivery of nutrients such as vitamins and minerals, enzymes and phytonutrients directly to the ceca to stimulate early gut development Delivery of fermentation products to the ceca which have been shown to stimulate water reabsorption, enteric development, and modulate the gut microbiome.

Delivery of vaccines (*cocci*, infectious bursal disease virus, Marek's disease virus, *salmonella*, etc.) and/or adjuvant agent that will modulate immunity or be used as immunotherapy.

Animals which may be treated by the methods of the presently disclosed subject matter are, in general, (non-mammalian) species having cloaca, such as birds. Any species of bird may be treated in accordance with the presently disclosed subject matter, including but not limited to chickens, turkeys, ducks, geese, quail, pheasant, and ratites. In addition to the production of food animals, the presently disclosed subject matter can also be used in conjunction with the raising of companion avian species, avian species in zoos, and endangered species such as the whooping crane to assist in efforts to preserve those species.

Early poultry nutrition plays a role in utilization of the yolk sac and development of a healthy gastrointestinal tract, including the establishment of the enteric microbiome that makes the bird more resistant to disease. Delivery of prebiotics (mannan-oligosaccharides, fructo-oligosaccharides, galacto-oligosaccharides, xylo-oligosaccharides, and cellulose), probiotics (commensal bacterial inoculates, direct-fed microbials, *Lactobacillus* sp., *Streptococcus* sp., *C. butyricum, Bacillus* sp.), nutrients (i.e. trace minerals, vitamins, organic acids, volatile fatty acids, and amino acids), osmolytes (e.g. betaine), vaccines (*cocci*, infectious bursal disease virus, Marek's disease virus, *salmonella*, etc.), and water to the chick or poult can prevent early mortality and improve productions parameters.

The digestive tract moves food through it using a muscular wave-like movement called peristalsis. Poultry also have the unique ability of reverse-peristalsis, meaning digesta can move backwards in the gastro-intestinal tract from the cloaca and colon to the ceca, from the ileum to the jejunum, from the jejunum to the duodenum, and from the duodenum into the gizzard-proventriculus. At the junction of the colon and the proximal ileum are two blind pouches, called ceca. The ceca are reservoirs for intestinal microbes and are also a major site, like the ileum, for water reabsorption.

Reverse-peristalsis gives birds the ability to pick up bacteria, protozoa, and parasites and fine particles from the litter and transport them back from the cloaca to the ceca where they grow and can cause serious spread of disease. Thus, provided in accordance with the presently disclosed subject matter is the utilization of the bird's natural ability of reverse-peristalsis to cloacally administer a solution comprising water, bio-active compounds, and/or nutrients to deliver it directly to the major sites of water reabsorption, thereby and enhancing the rehydration process of sick or dehydrated birds. This method is more effective than administering a water solution orally, which has to travel through most of the digestive tract before it is absorbed.

Hatchlings retain their yolk sac as a source of nutrient reserves, but the signal for young birds to absorb the nutrients in the yolk sac occurs when they first start eating. This means that due to the variability in hatching times and long transportation times, yolk sac resources my not be available to support enteric development for up to 24 hours after the chick hatches.

Cloacal administration of water and nutrients to the ceca and colon hydrates the birds for transportation, as well as stimulates yolk sac absorption and gut development. In order to enhance the effectiveness of this product a variety of nutrients will be suspended in a water solution, which will be cloacally administered to poultry. The bioactive compounds included in the solution individually or in combination may include, but not be limited to the following: vitamins, minerals and mineral complexes, amino acids and other amino compounds, peptides, carbohydrates and other oligosaccharides, organic acids, volatile fatty acids, osmolytes, pigments, enzymes, antioxidants, phytonutrients, fermentation products, galacto-proteins, and pre- and probiotics.

In some embodiments, birds, such as turkeys and chickens, are cloacally inoculated with various bacteria, protozoa and pathogens. Disease signs are observed on a regular basis, indicating that microorganisms can be delivered to the ceca. In some embodiments, the inoculant composition comprises a bacterial vector. In some embodiments, the inoculant composition is administered to test disease. In some embodiments, the inoculant composition is administered to test for colonization of the gut. In addition to probiotics and bacterial vector vaccines, protozoal vaccines, such as coccidiosis vaccines, can be administered. Currently, these *cocci* vaccines are given orally via gel or liquid spray on chicks at the hatchery or upon arrival on the farm, but the immune response of the chicks is variable depending on the actual dose each chick actually consumes. Some do not orally consume much of the gel or liquid spray with the *cocci* vaccine that is adhered to their feathers after application, if any, which leaves them susceptible to wild-type field *cocci* infections. Other chicks consume too much of the gel or liquid spray with the *cocci* vaccine, causing an over-dose of vaccine and consequently excessive immunological reactions and accompanying inflammation and damage of the enteric mucosal tissues that often leads to the disruption of the gut microbiome homeostasis and an imbalance of the microbiota, otherwise known as dysbiosis or dysbacteriosis.

There has been some attempted to deliver *cocci* vaccines in ovo, but this also has technical constraints. By way of example and not limitation, delivering *cocci* vaccines by vent delivers more precise dose for each bird more directly to the hind gut where these pathogens normally thrive and are in intimate contact with the cecal tonsils that sample antigens to mount immune response. In some embodiments, liposome, nanotube, or other colloidal system assembly protected vaccines using antigenic surface proteins, RNA or DNA fragments, or CpG-DONs that otherwise would not survive when oral or aerosol delivery are delivered. Non-vertebral DNA from protozoa, bacteria, and viruses contain higher amounts of unmethylated cytosine-phosphodiester-guanine (CpG) dinucfleotides as compared to eukaryotes (Hemmi et al., 2000, *Nature* 408, 740-745). These CpG DNA motifs are recognized as pathogen-associated molecular patterns (PAMP) by pattern recognition receptors (PRR), thereby inducing immune responses that prevent infections (Ahmad-Nejad et al., 2002, *Eur. J. Immunol.* 32: 1958-1968). Short oligodeoxynucleotides (ODNs) containing unmethylated CpG motifs (CpG ODNs) have been shown to be effective immunoprotective agents and vaccine adjuvants in mammalian systems, and a few studies have demonstrated their effectiveness to control enteric pathogens when injected in ovo to chicken embryos (Dalloul et al., 2005; *Vaccine* 23:3108-3113)).

The presently disclosed subject matter will now be described more fully hereinafter with reference to the accompanying Figures and EXAMPLES, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

I. DEFINITIONS

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

While the following terms are believed to be well understood by one of ordinary skill in the art, the following definitions are set forth to facilitate explanation of the presently claimed subject matter.

Following long-standing patent law convention, the terms "a", "an", and "the" refer to "one or more" when used herein, including in the claims.

As used herein, the term "about", when referring to a value or an amount, for example, relative to another measure, is meant to encompass variations of in some embodiments±20%, in some embodiments±10%, in some embodiments±5%, in some embodiments±1%, and in some embodiments±0.1% from the specified value or amount, as such variations are appropriate. The term "about" can be applied to all values set forth herein.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "and/of" when used in the context of a listing of entities, refers to the entities being present singly or in combination. Thus, for example, the phrase "A, B, C, and/or D" includes A, B, C, and D individually, but also includes any and all combinations and sub-combinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed in some embodiments as a "p-value". Those p-values that fall below a user-defined cutoff point are regarded as significant. In some embodiments, a p-value less than or equal to 0.05, in some embodiments less than 0.01, in some embodiments less than 0.005, and in some embodiments less than 0.001, are regarded as significant.

"Concurrently administering" as used herein refers to the administration of two separate compounds or compositions in close temporal proximity to one another (for example, simultaneously or sequentially). Concurrent administration may optionally be carried out by administering the two compounds or compositions together in a common carrier (e.g., by adding an enteric modulator to a bioactive composition comprising a nutrient).

"Synergistically" as used herein means that the combined effect of two separate active agents is greater than that which would be expected from the sum of the two agents when administered separately.

An "enteric modulator" as used herein refers to a compound that stimulates the development and/or metabolism of a cell of the digestive system, such cells including but not limited to enterocytes, goblet cells, intestinal lymphocytes, etc. Examples of suitable enteric modulators include, but are not limited to, 8-hydroxy-8-methylbutyrate (HMB), organic zinc complexes (Zn-amino acid complex, Zn-proteinate, Zn-chelates with a carbohydrate or protein or organic acid), lectins (Concanavalin A, Poke Weed Mitogen, Wheat Gluten Antigen, bean lectins, or lectins from microbial sources), glutamine or glutamate, arginine, carnitine, creatine, vitamins A, D, or E, betaine, choline, lecithin, S-adenosylmethionine, tyrosine and its metabolic derivatives (e.g. dopamine, norepinephrine, epinephrine), Tryptophan and its metabolic derivatives (e.g. serotonin, melatonin), glucosamine, fatty acid derivatives (omega-3 fatty acids, conjugated Linoleic acid, prostaglandins), and antioxidants (bioflavonoids, ascorbic acid, rutin, BHT, ethoxyquin, vitamin, pyrroloquinoline quinone and its derivatives, carotenoids). Beta-hydroxy-beta-methylbutyrate (HMB) (including the edible salts thereof) is known and disclosed in, among other references, U.S. Pat. No. 5,028,440 to Nissen, herein incorporated by reference in its entirety.

"Nutrient" as used herein refers to essential nutrients that are necessary for the growth of an animal to which they are fed. Nutrients include (a) proteins and protein fragments (e.g., peptides and amino acids such as lysine), (b) carbohydrates (sugars including monosaccharides, starches, dextrin, dextrose, oligosaccharides and polysaccharides), (c) lipids, etc.

In some embodiments, an effective amount of a bioactive composition of the presently disclosed subject matter is administered to a subject in need thereof. A "treatment effective amount" or "effective amount" as those phrases are used herein is an amount of a bioactive composition sufficient to produce a measurable response (e.g., a biologically or clinically relevant response in a subject being treated). Actual levels of an active agent or agents in the compositions of the presently disclosed subject matter can be varied so as to administer an amount of the active agent(s) that is effective to achieve the desired response for a particular subject. By way of example and not limitation an effective amount can range from about 0.5 mL/kg to about 7.5 mL/kg, including about 0.5, 1, 1.5, 2, 2.5, 3, 3.5, 4, 4.5, 5, 5.5, 6, 6.5, 7 and 7.5 mL/kg. By mL/kg, it is meant mL of bioactive composition solution per kg of live weight of subject. For smaller birds this can be on the higher dose side. By way of additional example and not limitation, the volume can be expressed relative to body mass, such ranging from about 0.01 to about 0.06 mL per gram of live body weight, including about 0.01, 0.02, 0.03, 0.04, 0.05 and 0.06 mL per gram of live body weight. In these embodiments, a 50 g chick given a volume of 0.02 ml/g will get a total of 1 ml volume, but a 500 g chick may get a volume of 10 ml. The volume capacity can also depend on the size of the bird's ceca. The concentration of the bioactive solution can vary based on the delivery amount needed. In some embodiments, for the purpose of rehydration, the bioactive solution composition should preferably not exceed about 300 mOsm. Particular components that can be included in the bioactive solution composition are at least about 0.05% sodium and 0.05% potassium.

The selected treatment effective amount can also depend upon combination with other drugs or treatments, the severity of the condition being treated, and the condition and prior medical history of the subject being treated. However, upon a review of the instant disclosure, it is within the skill of the art to start effective amounts of the compositions of the presently disclosed subject matter at levels lower than required to achieve the desired treatment effect and to gradually increase the effective amount until the desired treatment effect is achieved. The potency of a composition can vary, and therefore a "treatment effective amount" can vary. However, upon review of the instant disclosure one skilled in the art can readily assess the potency and efficacy of a bioactive composition of the presently disclosed subject matter and adjust the treatment regimen accordingly.

II. REPRESENTATIVE EMBODIMENTS

In accordance with the presently disclosed subject matter, provided is a method of delivering a bioactive composition to ceca of a bird. In some embodiments, the method comprises (a) providing a bioactive composition; (b) delivering a treatment effective amount of the bioactive composition to a cloaca of the bird; and (c) providing stimulation to a vent of the bird; whereby delivery of the bioactive composition to the ceca of the bird is accomplished. The bioactive composition can be in any form including liquids, solids, and combinations thereof, examples including but not limited to solutions, emulsions, suspensions, gels, etc. In some embodiments, the bioactive active compositions can comprise a liposome, a nanoparticle such as a nanotube, and/or any other vehicle as would be apparent to one of ordinary skill in the art upon a review of the instant disclosure. In some embodiments, the method comprises repeating steps (b) and (c) one or more times.

In some embodiments, the bioactive composition is water or comprises a water-based solution, suspension, gel, or emulsion. In some embodiments, the bioactive composition comprises a component selected from the group comprising a prebiotic (such as but not limited to a mannan-oligosaccharide, a fructo-oligosaccharide, a galacto-oligosaccharide, a xylo-oligosaccharide, cellulose, and any combination thereof), a probiotic (such as but not limited to a commensal bacterial inoculate, an anaerobic microbe, a direct-fed microbial, *Lactobacillus* sp, *Streptococcus* sp., *C. butyricum, Bacillus* sp., and any combination thereof), a nutrient (such as but not limited to a trace mineral, a vitamin, an organic acid, a volatile fatty acid, a carbohydrate, an amino acid, a peptide, a protein, and any combination thereof), an enteric modulator, an osmolyte (e.g. betaine), a vaccine (such as but not limited *cocci, salmonella*), fiber, water, and any combination thereof. A representative probiotic is disclosed in U.S. Pat. No. 5,308,615 to DeLoach et al., incorporated herein by reference in its entirety. A representative vaccine is disclosed in U.S. Pat. No. 2,910,407 to Hitchner et al., incorporated herein by reference in its entirety. In some embodiments, the bioactive composition comprises two or more components present in a synergistically effective amount.

In some embodiments, the bioactive composition contains from about one-half to about one hundred calories. In some embodiments, the total caloric composition of the bioactive composition will depend upon the particular species being treated, but will typically be at least about one-tenth, one, five, or ten calories up to twenty, forty, 100 or 200 calories, or more. For chickens and turkeys, the total caloric composition of the bioactive composition can be from about one-half or one to twenty or forty calories. In some embodiments, the osmotic pressure of the bioactive composition is not greater than about 800 millisomoles (mOsm), and can range from about 50, 100, 200 or 300 to about 600 or 700 milliosmoles. If the intent of the cloacal delivered solution is for hydration, it is preferable not to exceed 300 mOsm because that is the physiological osmotic pressure of the body fluids. If the cloacal delivered solution is greater than 300 mOsm, it can result in dehydration unless the birds has access to drinking water. However, if the intent of the cloacal delivered solution is for a purpose other than hydration without access to drinking water, then the bioactive composition can be up to 800 mOsm.

In some embodiments, the treatment effective amount comprises a volume of at least about 1 milliliter (mL). In some embodiments, the volume comprises an amount ranging from about 1 mL to about 3 mL, depending on the body mass of the treated animal. By way of example and not limitation an effective amount can range from about 0.1 mL/kg body mass to about 7.5 mL/kg body mass, including about 0.1, 0.5, 1, 1.5, 2, 2.5, 3, 3.5, 4, 4.5, 5, 5.5, 6, 6.5, 7 and 7.5 mL/kg. By mL/kg, it is meant mL of bioactive composition solution per kg of live weight of subject. By way of additional example and not limitation, the volume can be expressed relative to body mass, such ranging from about 0.01 to about 0.06 mL per gram of live body weight, including about 0.01, 0.02, 0.03, 0.04, 0.05 and 0.06 mL per gram of live body weight. In these embodiments, a 50 g chick given a volume of 0.02 mL/g will get a total of 1 mL volume, but a 500 g chick may get a volume of 10 mL. The volume capacity can also depend on the size of the bird's ceca.

In some embodiments, delivering a treatment effective amount of the bioactive composition to a cloaca of the bird comprises inserting a delivery device into the cloaca for a distance sufficient to provide delivery of the bioactive composition to the ceca. In some embodiments, the distance sufficient to provide for delivery of the bioactive composition to the ceca comprises about 0.25 to about 3 centimeters (cm), including about 0.25 to about 2 centimeters (cm). In some embodiments, the delivery device comprises a pipette or other blunt tubular device.

The presently disclosed methods can employ an intracloacal route to administer to administer probiotics and vaccines to evaluate induction of immunity against important enteric pathogens, including pathogenic clostridial bacteria and coccidian parasites. If it is planned to administer probiotics, a representative range for a treatment effective amount comprises about $1 \times 10^5$ to about $8 \times 10^9$ cfu, including about $1 \times 10^5$, $1 \times 10^6$, $1 \times 10^7$, $1 \times 10^8$, or $1 \times 10^9$ to about $8 \times 10^9$ cfu depending on the frequency of administration. In some embodiments, the probiotics that can colonize the intestines effectively can involve either single or two administrations; if the probiotics have poor colonizing ability, the frequency of administration can be increased to multiple (3-5) administrations given either daily or in weekly intervals. If it is desired to provide a bacterial vector-based vaccine, a representative amount starts at $1 \times 10^8$ cfu for a certain period of time, such as but not limited to ranging over about 1 to about 7 days post hatch, including about 2, 3, 4, 5, 6 days post hatch. This time period can include single administration at day of hatch or administered at multiple time points during bird's life to achieve desired effect. For bacterial vectors with efficient gut colonization ability, $1 \times 10^8$ cfu may provide an effective dosage, while for other vectors with poor to moderate colonization ability, higher cfu dose may be employed. A representative formulation for a probiotic or vaccine can comprises an active agent and a protective biological to deliver the active ingredient, about 0.25 to about 3 centimeters (cm) into the cloaca. In some embodiments, the bioactive active composition can comprise a liposome (see Sercombe et al., *Front. Pharmacol.,* 1 Dec. 2015, pp. 1-13; see also U.S. Pat. Nos. 10,456,459; 7,037, 501, each of which are herein incorporated by reference in its entirety), a carbon nanotube (see Zare et al., 2021, *International Journal of Nanomedicine* 2021:16 1681-1706; U.S. Pat. No. 10,022,435, herein incorporated by reference its entirety), and/or any other protective biological vehicle as would be apparent to one of ordinary skill in the art upon a review of the instant disclosure. See also Renu and Renukaradhya, *Front Bioeng Biotechnol.* 2020 Nov. 13; 8:558349; Muir et al., *Dev Comp Immunol.* March-April 2000; 24(2-3):325-42; and Jin et al, *Int J Pharm.* 2019 Dec. 15; 572; see also U.S. Pat. No. 9,878,036, herein incorporated by reference its entirety. In some embodiments, a vaccine containing a bacterial culture as described above can be used at the research level. In some embodiments, a probiotic or vaccine can be administered in encapsulating bacteria in a suitable biomolecule (for example, nanoparticles and/or liposomes, and the like) to enhance the delivery of these bacteria in the gut compartments. Again, a representative range for bacterial vaccine purposes comprises a range of $1 \times 10^8$-$5 \times 10^9$ cfu of bacteria.

In some embodiments, the presently disclosed subject matter provides a probiotic developed for a particular disease for delivery through the vent as a combination product-probiotic plus vaccine. In some embodiments, the probiotic expresses an antigen of interest that would mount immunological protection against a pathogenic agent (see da Silva et al., 2014, *Braz. J. Microbiol.* 45 (4) •December 2014 and Yurina, 2018, *Med. Sci.* 2018, 6(2), 27). In some embodiments, the presently disclosed subject matter provides a probiotic developed for a particular disease for delivery through the vent as a disease prevention product or administered in combination with a commercially available mucosal vaccine product, such as the Infectious Bronchitis virus, *Salmonella* or Coccidiosis vaccines (Wilson et al., 2020, *Mucosal Vaccines* 2020:811-829). In some embodiments, the recombinant probiotic isolate expressing heterologous antigen(s) of interest that can target a specific disease control. Representative mucosal formulation approaches are disclosed in U.S. Pat. No. 10,258,688, herein incorporated by reference in its entirety. Other representative probiotic and/or vaccine preparation and formulation techniques are described in U.S. Pat. Nos. 10,624,366; 10,022,435; 9,884,099; 9,580,718; 9,393,275; 8,465,755; and 8,431,138, each of which are herein incorporated by reference in its entirety.

In some embodiments, provided are protein-based vaccine formulations to immunize chickens to evaluate immunity against *C. perfringens*-induced necrotic enteritis disease; probiotics formulations for chickens to prevent the occurrence of *C. perfringens*-induced necrotic enteritis disease; and probiotic-based recombinant vaccine formulations for the control of necrotic enteritis in chickens and clostridial dermatitis disease in turkeys. In some embodiments, the vaccine and the probiotic are provided in combination-probiotic plus vaccine.

In some embodiments, the bird is selected from the group comprising chickens, turkeys, ducks, geese, quail, pheasant, and ratites (including but not limited to ostrich, rheas, and emus). In some embodiments, the bird is treated prior to, during, and/or after transport.

In accordance with the presently disclosed subject matter, provided is a bioactive composition adapted for cloacal administration to a bird in need of receiving treatment by the bioactive composition. In some embodiments, the bioactive composition comprises two or more components selected from the group comprising a prebiotic (such as but not limited to a mannan-oligosaccharide, a fructo-oligosaccharide, a galacto-oligosaccharide, a xylo-oligosaccharide, cellulose, and any combination thereof), a probiotic (such as but not limited to a commensal bacterial inoculate, an anaerobic microbe, a direct-fed microbial, *Lactobacillus* sp, *Streptococcus* sp., *C. butyricum, Bacillus* sp., and any combination thereof), a nutrient (such as but not limited to a trace mineral, a vitamin, an organic acid, a volatile fatty acid, a carbohydrate, an amino acid, a peptide, a protein, and any combination thereof), an enteric modulator, an osmolyte (e.g. betaine), a vaccine (such as but not limited *cocci, salmonella*), fiber, water, and any combination thereof, wherein at least one of the two or more components is present in a treatment effective amount. In some embodiments, the bioactive composition comprises two or more components present in a synergistically effective amount.

In some embodiments, the bioactive composition contains from about one-half to about one hundred calories. In some embodiments, the total caloric composition of the bioactive composition will depend upon the particular species being treated, but will typically be at least about one-tenth, one, five, or ten calories up to twenty, forty, 100 or 200 calories, or more. For chickens and turkeys, the total caloric composition of the bioactive composition can be from about one-half or one to twenty or forty calories. In some embodiments, the osmotic pressure of the bioactive composition is not greater than about 800 millisomoles (mOsm), and can range from about 50, 100, 200 or 300 to about 600 or 700 milliosmoles. If the intent of the cloacal delivered solution is for hydration, it is preferable not to exceed 300 mOsm because that is the physiological osmotic pressure of the body fluids. If the cloacal delivered solution is greater than 300 mOsm, it can result in dehydration unless the birds has access to drinking water. However, if the intent of the cloacal delivered solution is for a purpose other than hydration without access to drinking water, then the bioactive composition can be up to 800 mOsm.

In some embodiments, the treatment effective amount comprises a volume of at least about 1 milliliter (mL). In some embodiments, the volume comprises an amount ranging from about 1 mL to about 3 mL, depending on the body mass of the treated an. By way of example and not limitation an effective amount can range from about 0.1 mL/kg to about 7.5 mL/kg, including about 0.1, 0.5, 1, 1.5, 2, 2.5, 3, 3.5, 4, 4.5, 5, 5.5, 6, 6.5, 7 and 7.5 mL/kg. By mL/kg, it is meant mL of bioactive composition solution per kg of live weight of subject. By way of additional example and not limitation, the volume can be expressed relative to body mass, such ranging from about 0.01 to about 0.06 mL per gram of live body weight, including about 0.01, 0.02, 0.03, 0.04, 0.05 and 0.06 mL per gram of live body weight. In these embodiments, a 50 g chick given a volume of 0.02 ml/g will get a total of 1 ml volume, but a 500 g chick may get a volume of 10 ml. The volume capacity can also depend on the size of the bird's ceca. In some embodiments of a composition of the presently disclosed subject matter, a variety of nutrients are dissolved and/or suspended in a water-based solution, which are cloacally administered to poultry. The bioactive compounds included in the solution individually or in combination include, but are not be limited to, the following: vitamins, minerals and mineral complexes, amino acids and other amino compounds, peptides, carbohydrates and other oligosaccharides, organic acids, volatile fatty acids, osmolytes, pigments, enzymes, antioxidants, phytonutrients, fibers and cellulose products, fermentation products, galacto-proteins, prebiotics and probiotics, and vaccines.

In some embodiments, a composition of the presently disclosed subject matter is provided in a formulation for hydration. To elaborate, the bird's natural ability of reverse-peristalsis is utilized to cloacally administer an aqueous composition, such as a solution and/or suspension comprising water, bio-active compounds, and/or nutrients for delivery directly to the major sites of water reabsorption (which include the ceca), thereby enhancing the rehydration process of sick or dehydrated birds. This method is more effective than administering a water solution orally, which has to travel through most of the digestive tract before it is absorbed. The bioactive compounds included in the hydration solution individually or in combination can include, but are not limited to the following: water, saline, fermentation products (such as but not limited to acetate, butyrate, and/or propionate), fiber and cellulose products, vitamins, minerals and mineral complexes, carbohydrates and other oligosaccharides, organic acids, volatile fatty acids, osmolytes and prebiotics and probiotics. Although the base formula can be the same for all species, the formula can also be adapted for each species, based on the physiological needs of the species and on the application purpose for the species to be treated.

When birds become dehydrated during stress or long transportation, they become lethargic and lose their ability to find food or water, which can ultimately lead to death. Hydrating chicks and poults, before they are transported long distances, decreases mortality, which is an economical and welfare benefit for the farmer. Hatchlings retain their yolk sac as a source of nutrient reserves, but the signal for young birds to absorb the nutrients in the yolk sac occurs when they first start eating. This means that due to the variability in hatching times and long transportation times, yolk sac resources my not be available to support enteric development for up to 24 hours after the chick hatches. Cloacal administration of water and nutrients to the ceca and colon hydrate the birds for transportation, as well as stimulate yolk sac absorption and gut development. Birds, like layers and breeders, can also become dehydrated later in life due to stress or environmental factors. Administering a hydration solution cloacally to these birds would rehydrate them more effectively than giving them a solution orally and could decrease mortality.

In some embodiments, a composition of the presently disclosed subject matter is provided in a formulation for probiotics/prebiotics. To elaborate, the bird's natural ability of reverse-peristalsis is utilized to cloacally administer a composition (such as a solution and/or suspension) comprising prebiotics, probiotics, and/or nutrients for delivery directly to the ceca, the location of the GIT which houses most microbes and where most microbial fermentation occurs. This method is more effective than administering prebiotics and probiotics orally, which have to travel through most of the digestive tract before they reach the ceca. The bioactive compounds included in a prebiotic/probiotic solution individually or in combination can include, but are not limited to the following: prebiotics (e.g., mannan-oligosaccharides, fructo-oligosaccharides, galacto-oligosaccharides, xylo-oligosaccharides, and cellulose), probiotics (e.g., commensal bacterial inoculates, direct-fed microbials, *Lactobacillus* sp., *Streptococcus* sp., *C. butyricum, Bacillus* sp.), vitamins, carbohydrates and/or other oligosaccharides, organic acids, volatile fatty acids, fibers and cellulose products, and/or fermentation products. Although the base formula can be the same for all species, the formula can be adapted for each species, based on the physiological needs of the species and on the application purpose for the species.

In some embodiments, a composition of the presently disclosed subject matter is provided in a formulation for vaccines. To elaborate, the bird's natural ability of reverse-peristalsis is utilized to cloacally administer vaccines for delivery directly to the lower GIT and ceca. This method can be more effective than alternate methods of administering vaccines due to the close proximity of the ceca and the bursa of Fabricius, a specialized immune organ in poultry. The vaccines included in the solution individually or in combination can include, but are not limited to the following: coccidiosis, infectious bursal disease virus, Marek's disease virus, *salmonella* and/or necrotic enteritis. Any vaccine for use in poultry can be administered this way. This includes vaccination of exotic birds or pet birds.

The presently disclosed bioactive composition can be adapted for administration via an intra-cloacal route to administer to administer probiotics and/or vaccines to evaluate induction of immunity against important enteric pathogens, including pathogenic clostridial bacteria and coccidian parasites. If it is planned to administer probiotics, a representative range for a treatment effective amount comprises about $1\times10^5$ to about $8\times10^9$ cfu, including about $1\times10^5$, $1\times10^6$, $1\times10^7$, $1\times10^8$, or $1\times10^9$ to about $8\times10^9$ cfu depending on the frequency of administration. In some embodiments, the probiotics that can colonize the intestines effectively can involve either single or two administrations; if the probiotics have poor colonizing ability, the frequency of administration can be increased to multiple (3-5) administrations given either daily or in weekly intervals. If it is desired to provide a bacterial vector-based vaccine, a representative amount starts at $1\times10^8$ cfu for a certain period of time, such as but not limited to ranging over about 1 to about 7 days post hatch, including about 2, 3, 4, 5, 6 days post hatch. This time period can include single administration at day of hatch or administered at multiple time points during bird's life to achieve desired effect. For bacterial vectors with efficient gut colonization ability, $1\times10^8$ cfu may provide an effective dosage, while for other vectors with poor to moderate colonization ability, higher cfu dose may be employed. A representative formulation for a probiotic or vaccine can comprises an active agent and a protective biological to deliver the active ingredient, about 0.25 to about 3 centimeters (cm) into the cloaca. In some embodiments, the bioactive active composition can comprise a liposome (see Sercombe et al., *Front. Pharmacol.,* 1 Dec. 2015, pp. 1-13; see also U.S. Pat. Nos. 10,456,459; 7,037,501, each of which are herein incorporated by reference in its entirety), a carbon nanotube (see Zare et al., 2021, International Journal of Nanomedicine 2021:16 1681-1706; U.S. Pat. No. 10,022, 435, herein incorporated by reference its entirety), and/or any other protective biological vehicle as would be apparent to one of ordinary skill in the art upon a review of the instant disclosure. See also Renu and Renukaradhya, *Front Bioeng Biotechnol.* 2020 Nov. 13; 8:558349; Muir et al., *Dev Comp Immunol.* March-April 2000; 24(2-3):325-42; and Jin et al, *Int J Pharm.* 2019 Dec. 15; 572; see also U.S. Pat. No. 9,878,036, herein incorporated by reference its entirety. In some embodiments, a vaccine containing a bacterial culture as described above can be used at the research level. In some embodiments, a probiotic or vaccine can be administered in encapsulating bacteria in a suitable biomolecule (for example, nanoparticles and/or liposomes, and the like) to enhance the delivery of these bacteria in the gut compartments. Again, a representative range for bacterial vaccine purposes comprises a range of $1\times10^8$-$5\times10^9$ cfu of bacteria.

In some embodiments, the presently disclosed subject matter provides a probiotic developed for a particular disease for delivery through the vent as a combination product-probiotic plus vaccine. In some embodiments, the probiotic expresses an antigen of interest that would mount immunological protection against a pathogenic agent (see da Silva et al., 2014, *Braz. J. Microbiol.* 45 (4) •December 2014 and Yurina, 2018, *Med. Sci.* 2018, 6(2), 27). In some embodiments, the presently disclosed subject matter provides a probiotic developed for a particular disease for delivery through the vent as a disease prevention product or administered in combination with a commercially available mucosal vaccine product, such as the Infectious Bronchitis virus, *Salmonella* or Coccidiosis vaccines (Wilson et al., 2020, *Mucosal Vaccines* 2020:811-829). In some embodiments, the recombinant probiotic isolate expressing heterologous antigen(s) of interest that can target a specific disease control. Representative mucosal formulation approaches are disclosed in U.S. Pat. No. 10,258,688, herein incorporated by reference in its entirety. Other representative probiotic and/or vaccine preparation and formulation techniques are described in U.S. Pat. Nos. 10,624,366; 10,022,435; 9,884,099; 9,580,718; 9,393,275; 8,465,755; and 8,431,138, each of which are herein incorporated by reference in its entirety.

In some embodiments, provided are protein-based vaccine formulations to immunize chickens to evaluate immunity against *C. perfringens*-induced necrotic enteritis disease; probiotics formulations for chickens to prevent the occurrence of *C. perfringens*-induced necrotic enteritis disease; and probiotic-based recombinant vaccine formulations for the control of necrotic enteritis in chickens and clostridial dermatitis disease in turkeys. In some embodiments, the vaccine and the probiotic are provided in combination-probiotic plus vaccine.

Any suitable methods of use related to the product/ formulations described above can be employed in accordance with the presently disclosed subject matter. By way of example and not limitation, the following technique can be used to administer any composition, e.g. liquid solution, suspension or emulsion, to inside the cloaca of all poultry species. The user employs gloves, a delivery device (such as any blunt tubular device that can inserted into the vent at least about 0.25 cm to about 3 cm, including about 0.25 cm to about 2 cm, depending on the size of the bird and the amount (e.g., volume) of composition to be delivered; e.g. a pipette) and the composition to be cloacally delivered. First, prepare the composition for delivery with a sufficient amount (e.g., volume) for each bird, plus some extra. Second, another user holds the bird upside down by the feet and waits for it to relax and stop flapping its wings. Third, the user inserts the delivery device (e.g., a pipette tip) approximately about 0.25 cm to about 3 cm into the cloaca, deposits a selected amount (e.g., volume) of the composition to inside the cloaca, and removes the delivery device. Fourth, with a gloved finger, the user gently taps the outside of the cloaca to stimulate movement of the vent and ensure the liquid is taken up. Finally, birds are desirably held upside down in that position at least about 2 minutes to allow the reverse peristalsis motion to transport the composition to the ceca, although an amount of time less than about 2 minutes can be employed. In some embodiments, an amount of time ranging from about 1 minute to about 5 minutes can be employed.

The above method utilizes the birds' reverse-peristalsis capability for targeted delivery of a given substance to the upper colon and ceca of any poultry species. Many feed additives meant to improve bird health and performance are intended to reach the ceca but have to travel through the entire GIT first where nutrient interaction and degradation occur. By cloacally administering a substance, it allows the bioactive nutrients immediate access to the ceca and cecal contents without being exposed to the entire GIT first. This technique can also be utilized for delivery of a probiotic or vaccine.

Any liquid composition, e.g. solution, suspension, or emulsion, can also be administered by saturating an absorbable material (e.g., a sponge-like material or transport shavings) with the composition and placing under the birds (e.g. during transport). The composition is taken up by the birds through their cloaca when they sit on it and reverse peristalsis delivers the bioactive ingredients to the ceca. By way of particular example, this technique can be utilized for delivery of a probiotic and/or vaccine since it can be use with large numbers of birds at one time. Although the base formula can be the same for all species, the formula can be adapted for each species, based on the physiological needs of the species and application purpose for the species.

The presently disclosed subject matter can be used as a hydration product for chicks, poults, and any other avian species, as well as a rehydration product for adult birds (layers and breeders). Cloacally administering a solution for targeted delivery to the ceca can be used for effective cecal product delivery, bypassing the upper GIT, which can be used for treatment delivery against cecal pathogens. This can be used for the delivery of nutrients, prebiotics, probiotics and/or vaccines to the upper colon or ceca. The presently disclosed subject matter can also be used to help rehabilitate or rehydrate sick birds. Birds who are diseased often are too weak to access water and food and therefore become dehydrated and weaker which can lead to death. If farmers are able to administer a product to sick looking birds to hydrate them and help them regain energy, it will improve welfare and overall mortality. In addition, the presently disclosed subject matter can applied to exotic birds at zoos, aviaries, pet shops, veterinary clinics, and personal residences. The presently disclosed subject matter can be used to delivery any liquid solution or non-liquid material suspended in a liquid solution to inside the cloaca of any avian species and use the bird's reverse peristalsis capability to target deliver the solution and bioactive nutrients to the upper colon or ceca.

Administering a composition cloacally speeds up the rehydration process by delivering the water directly to the sites of water reabsorption in the bird. The presently disclosed subject matter also prevents nutrient interaction in the crop, gizzard, proventriculus and small intestine by completely bypassing the upper digestive tract. After they hatch, young chicks and poults are very often transported long distances in stressful conditions to their final housing destination. This often causes dehydration and a lack of nutrients at a critical age. If chicks and poults are cloacally given a dose of water, nutrients, prebiotics and/or probiotics, it hydrates them for the long transportation, and also stimulates gut development and encourages the colonization of commensal microbes in the ceca to reduce the chance of enteric disease.

III. EXAMPLES

The following EXAMPLES provide illustrative embodiments. In light of the present disclosure and the general level of skill in the art, those of skill will appreciate that the following EXAMPLES are intended to be exemplary only and that numerous changes, modifications, and alterations can be employed without departing from the scope of the presently disclosed subject matter.

Example 1

This EXAMPLE involved feeding pure cellulose cotton fibers to turkeys at a 1%, 5% and 10% inclusion level in the diet for 3 days in a small pilot trial. A pipette was used as the administration device. One (1) milliliter (mL) of a water-based suspension was administered to each bird.

After sampling the cecal contents of the birds, the cecal samples were successfully spun down. Cotton linter fibers were isolated from the samples in each treatment and viewed under a microscope. The fibers appeared to be mostly intact and undigested. The 5% inclusion level seemed to result in the most ideal balance of feed intake and the concentration of fiber found in the ceca. But, 5% typically is too high of a fiber inclusion level for commercial diets.

Turkeys were also cloacally inoculated with these fibers mixed with water. About 3 hours were allowed for the turkeys' reverse peristalsis ability of the lower digestive tract to carry the fibers to the ceca. Then, the cecal contents were sampled and successfully spun down. The fibers were microscopically isolated.

Thus, the EXAMPLE demonstrates that cotton cellulose fibers can be delivered to the ceca from the cloaca of a bird and that the fibers can be isolated, intact, from the cecal contents.

Example 2

This EXAMPLE involved cloacally administering a hydration solution (1 g acetate/100 mL water) to dehydrated day-old turkey poults in a small pilot trial. A pipette was used as the administration device. The poults became dehydrated during transport to the farm and upon arrival at the farm birds were cloacally given 2 mL of either the hydration solution or water. After 4-6 hours the birds were evaluated. Of the 12 birds given just water, three (3) recovered. Of the 12 birds given the hydration solution, seven (7) recovered.

Example 3

The following are species/age combinations that were tested for the average maximum (avg max) amount of solution that could be put into the cloaca of the bird (n=5 birds per species/age combo).

Turkey/1 day→avg max 1.5-2 mL
Turkey/3 weeks→avg max 5-7 mL
Turkey/15 weeks→avg max 12-14 mL
Broiler/1 day→avg max 1.5-2 mL
Broiler/6 weeks→avg max 8-10 mL

Example 4

Introduction. The ceca (like the large intestine) is a major site for short-term water retention and water reabsorption in the bird. Water and small undigested particles enter the avian ceca, are fermented and then the water is reabsorbed resulting in a thick, dark paste that is excreted as a cecal dropping. Birds can become dehydrated due to long transportation times or illness on the farm and administration of water and water absorption enhancement products, such as acetate, could help improve mortality. Literature suggests that the addition of acetate to the cecal contents significantly increases water absorption of the bird. Acetate happens to be one of the main byproducts of cecal microbial fermentation (along with butyrate and propionate) and may be one signal to the ceca to absorb the remaining water post-fermentation, aiding in the cycling of the ceca. It is common practice for poults to be placed in poultry houses as long as 48+ hours after hatching, due to long transportation times.

This EXAMPLE relates to the study of water absorption related to hydration of young turkeys. 300 one-day-old turkey poults were obtained from a commercial hatchery and split into 5 treatment groups with 6 pens per treatment (10 birds/pen). One group (T1, Treatment 1 in FIG. 1) served as the control and was placed as soon as they arrive at the farm from the hatchery. The second group (T2, Treatment 2 in FIG. 1) was held without feed or water for 48 hours before placement. The third group (T3, Treatment 3 in FIG. 1) was cloacally administered 1 mL of a solution of water and acetate (1 g acetate/100 mL water) upon arrival to the farm and then placed. The fourth group (T4, Treatment 4 in FIG. 1) was cloacally administered the same solution of water and acetate upon arrival to the farm, held for 48 hours and then placed. The final group (T5, Treatment 5 in FIG. 1) was held for 48 hours, cloacally administered the solution of water and acetate and then placed. During the holding time before placement birds were at 90 degrees Fahrenheit. Upon placement, all birds had ad libitum access to water and control feed. Each bird was weighed upon arrival at the farm (D0), before placement (D2) and on days (D) 7, 14 and 21 to determine how poult hydration quality affects body weight gain of turkey poults. In the industry, poults are normally set in the house between 12-72 hours post-hatch. Longer times between hatch and placement have been suggested to cause problems with gut development caused by delayed feed and water intake. The above research will determine the effects of delayed placement used in the industry and if cloacal administration of a water and acetate solution can improve poultry quality and early growth parameters.

Results. Table 1 contains the mean body weights (kg) by treatment. Upon arrival to the farm (D0) all treatment groups had statistically equivalent mean poult body weights. After the 48 hour hold for T2, T4 and T5 birds in those treatment groups had significantly lower mean body weights than birds in the control treatment (T1) and T3. Birds in treatments 2, 4 and 5 had body weights significantly lower that birds in T1 or T3 for the remained of the 3 week trial, showing that in this situation poult dehydration can lead to decreased body weights at 3 weeks of age, regardless of the timing of the acetate/water treatment.

TABLE 1

| | Mean body weights (kg) by treatment | | | | |
|---|---|---|---|---|---|
| Treatment | D 0 | D 2 | D 7 | D 14 | D 21 |
| 1 | .0593[a] | .0664[a] | .1175[a] | .2450[a] | .4483[a] |
| 2 | .0589[a] | .0511[b] | .0857[b] | .2017[b] | .3877[b] |
| 3 | .0586[a] | .0654[a] | .1132[a] | .2359[a] | .4324[a] |
| 4 | .0588[a] | .0512[b] | .0862[b] | .2011[b] | .3925[b] |
| 5 | .0593[a] | .0514[b] | .0849[b] | .1983[b] | .3820[b] |
| SEM | .0004 | .0005 | .002 | .004 | .008 |
| p-value | .7587 | <.0001 | <.0001 | <.0001 | <.0001 |

Treatment means within a column with a different letter superscript are highly significantly different (P<0.0001).

FIG. 1 contains a histogram of the mortalities by treatment. Treatment 3 had the lowest mortality indicating that a 1 mL acetate/water cloacal inoculation directly prior to placement may reduce mortality during the first 3 weeks of turkey production. Treatment 4 had the highest mortality indicating that a 1 mL acetate/water cloacal inoculation prior to a long dehydration stress does not reduce mortality.

Example 5

After looking more closely at how the cecal cycle functions, in this EXAMPLE, additives are explored that can manipulate the cecal environment to help advance the health of the birds. Fiber is nondigestible and, at a small enough particle size, is directed into the ceca to be fermented. Some literature suggests that higher inclusion levels of fiber in poultry feed may result in better cecal function (more fermentation and water reabsorption). The typical poultry diet contains very little fiber because it does not directly deliver any nutritional value to the bird. But, it may aid in cecal functioning, which could improve water retention and improve bird health. Fiber has the potential to be utilized as a delivery mechanism, directly to the ceca, for antimicrobial agents like oils and minerals, allowing bioactive ingredients to be used at lower levels. The fiber products that are evaluated include: wheat bran, cotton cellulose fibers, cotton bur fibers at 3 different grind sizes (dust, 100 mesh screen and 300 mesh screen, cotton bur fibers+cottonseed oil. For the following experiments, fiber products are included in the diet at no more than 5%, which is within normal commercial levels for all poultry species. No products used are uncommon ingredients in poultry diets.

Experiments are each be performed once for each fiber product. In one experiment, it is evaluated whether the product reaches the ceca. This involves evaluating whether each product is delivered to the ceca via oral and/or cloacal delivery. To do this, 20 one-day old turkey poults are placed in 4 battery cages (5 birds/pen). 3 cages have ad libitum access to water and feed containing either a 0%, 1% or 5% inclusion level of one of the fiber products. In the fourth battery cage, birds have ad libitum access to water and control feed containing no product. All birds in this pen are cloacally inoculated with a solution containing distilled water and the fiber product on day 7. Three hours after the cloacal inoculation, all birds from each treatment are humanely euthanized and their cecal contents are collected, microscopically analyzed, and scored on a subjective scale measuring fiber concentration.

In another experiment, it is evaluated how does the product affects the cecal microbiome. To elaborate, whether there are any beneficial cecal microbiota shifts caused by the product is evaluated. To do this, 144 one-day old turkey poults are divided into 3 treatment groups with 4 pens per treatment (12 birds per pen). The treatments comprise either a 0%, 1% or 5% product inclusion level in the feed. Birds are placed in battery cages and given ad libitum access to water and feed. On days 7, 14 and 28, birds from each treatment (4 birds per pen) are humanely euthanized and their cecal contents are microscopically analyzed, scored, and sampled for microbiome analysis.

Example 6

This EXAMPLE relates to cloacal administration to 15 3-week-old turkey poults of 2 mL of a dyed water solution. Birds were culled 5 minutes later and their cecal contents were examined for presence of the dye. The dye was visible in the ceca of all 15 birds.

Figure 2:
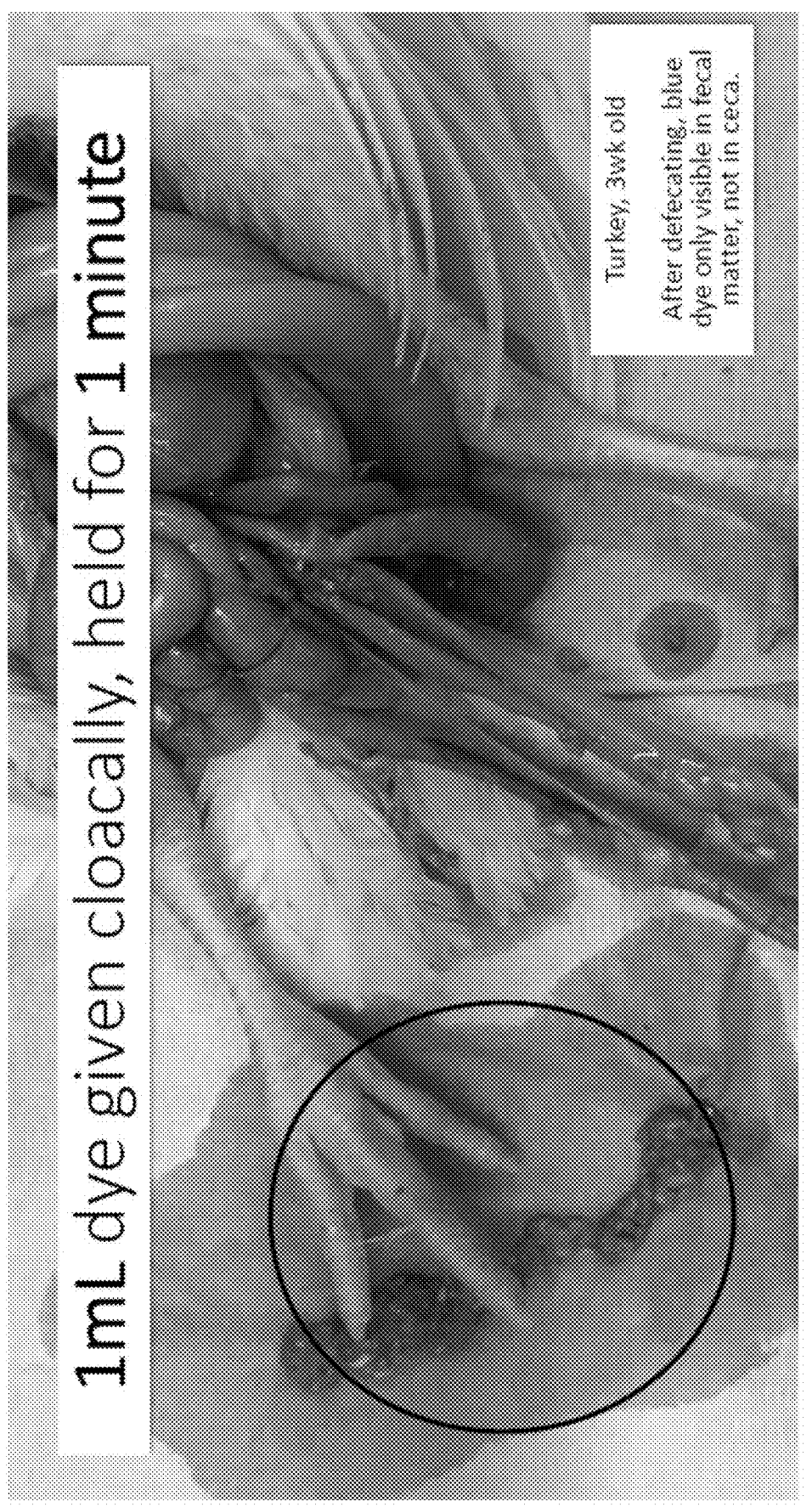
FIGS. 2-6 are color photographs showing cloacal administration to 3-week-old turkey poults of 2 mL of a dyed water solution, as described in EXAMPLE 6 below.
Figure 3:

Referring to FIGS. 2 to 6, shown are turkey ceca where a solution was given cloacally. The solution was water and blue dye. The concentration for the water:dye solution was 10:1. Experimental variables included how long the bird was held upside down prior to being culled (to encourage reverse peristalsis), and how far in the ceca the blue dye was observed after the bird was culled and necropsied. The procedure employed was as follows:

1. Birds were held upside down by their feet and the appropriate amount of the blue dye water solution was administered cloacally.
2. Birds were then held upside down in that position for the appropriate amount of time.
3. Birds were placed on a sheet of paper and allowed to defecate.
4. After defecating, birds were humanely culled and necropsied.
5. Pictures were taken and the ceca were examined for how far into the cecal lumen the blue dye was visible. An aspect of this EXAMPLE is to show that an increase in volume and/or time increased the distance that the solution went into the ceca. The baseline pictures are FIGS. 2 and 3, showing that 1 mL of the solution for 1 minute allowed the solution to enter the colon of the bird, but the bird could just defecate when placed back down in their pens and most of the solution would come out, leaving little or none in the ceca. In the following pictures, it is shown that an increase in time (5 min) and or volume (5 mL) allowed the solution to be pushed further into the ceca, ensuring a better and more effective delivery.

Referring to FIG. 2, 1 mL aqueous dye solution was given cloacally and the subject was held upside down for 1 minute. The subject was a three-week old turkey. After defecating, blue dye only visible in fecal matter, not in ceca. Referring to FIG. 3, 1 mL aqueous dye solution was given cloacally and the subject was held upside down for 1 minute. The subject was a three-week old turkey. After defecating, blue dye was visible in the top quarter of the cecal tonsils (in the colon and about ¼ inch into the ceca).

Figure 4:
Figure 5:
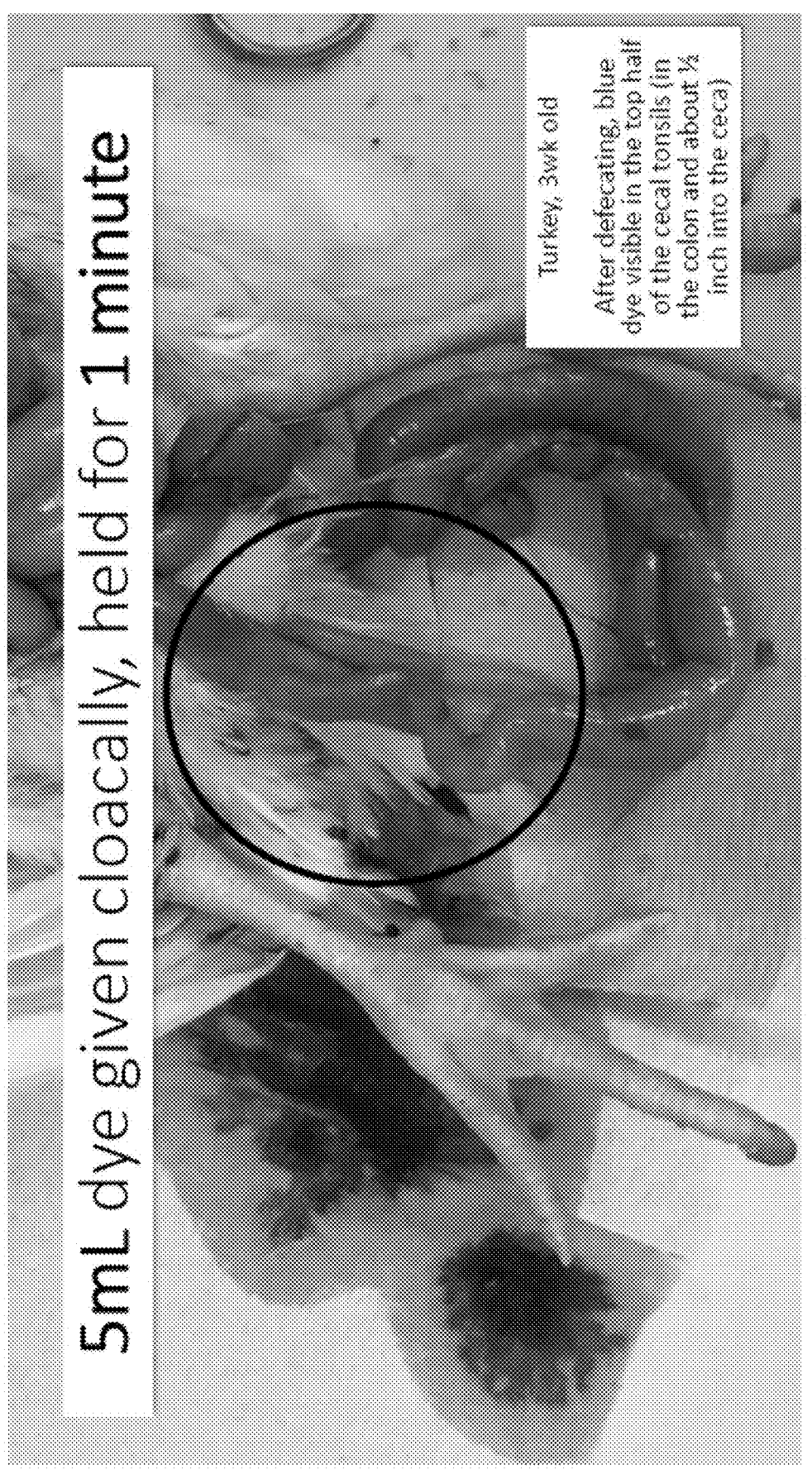
Figure 6:

Referring to FIG. 4, 5 mL aqueous dye solution was given cloacally and the subject was held upside down for 5 minutes. The subject was a three-week old turkey. After defecating, blue dye is visible in the cecal tonsils (in the colon and about 1 inch into the ceca). Referring to FIG. 5, 5 mL aqueous dye solution was given cloacally and the subject was held upside down for 1 minute. The subject was a three-week old turkey. After defecating, blue dye was visible in the top half of the cecal tonsils (in the colon and about 12 inch into the ceca). Referring to FIG. 6, 1 mL aqueous dye solution was given cloacally and the subject was held upside down for 5 minutes. The subject was a three-week old turkey. After defecating, blue dye was visible in the top half of the cecal tonsils (in the colon and about 1%2 inch into the ceca).

Summarily, it can be seen from FIGS. 2-6 that the longer (time) birds are held upside down and the more (volume) solution they are given cloacally, the better the delivery is to the cecal lumen.

Example 7

Evaluation of Administering Biological Agents Via Intra-Cloacal (Vent Drinking) Route in Chickens

Experiment 1: Administering Black Dye (Food Color)

Two-week-old broiler chickens (n=3) were administered with the dye while the control birds (n=3) received distilled water. The cloacal administration was performed as described below:

With the bird held upside-down gently in one hand, a pre-lubricated 3-inch cannula with a rounded tip or a blunt plastic cannula designed to avoid any mucosal injury was passed gently through the cloaca approximately ½-1 inch to deliver 0.5 mL of the dye. The outside of the cloaca was gently tapped to stimulate movement of the vent (cloacal drinking) and the reverse peristalsis motion. The birds were then held in an upside-down position briefly before putting them back into their pens.

Figures 7A, 7B:
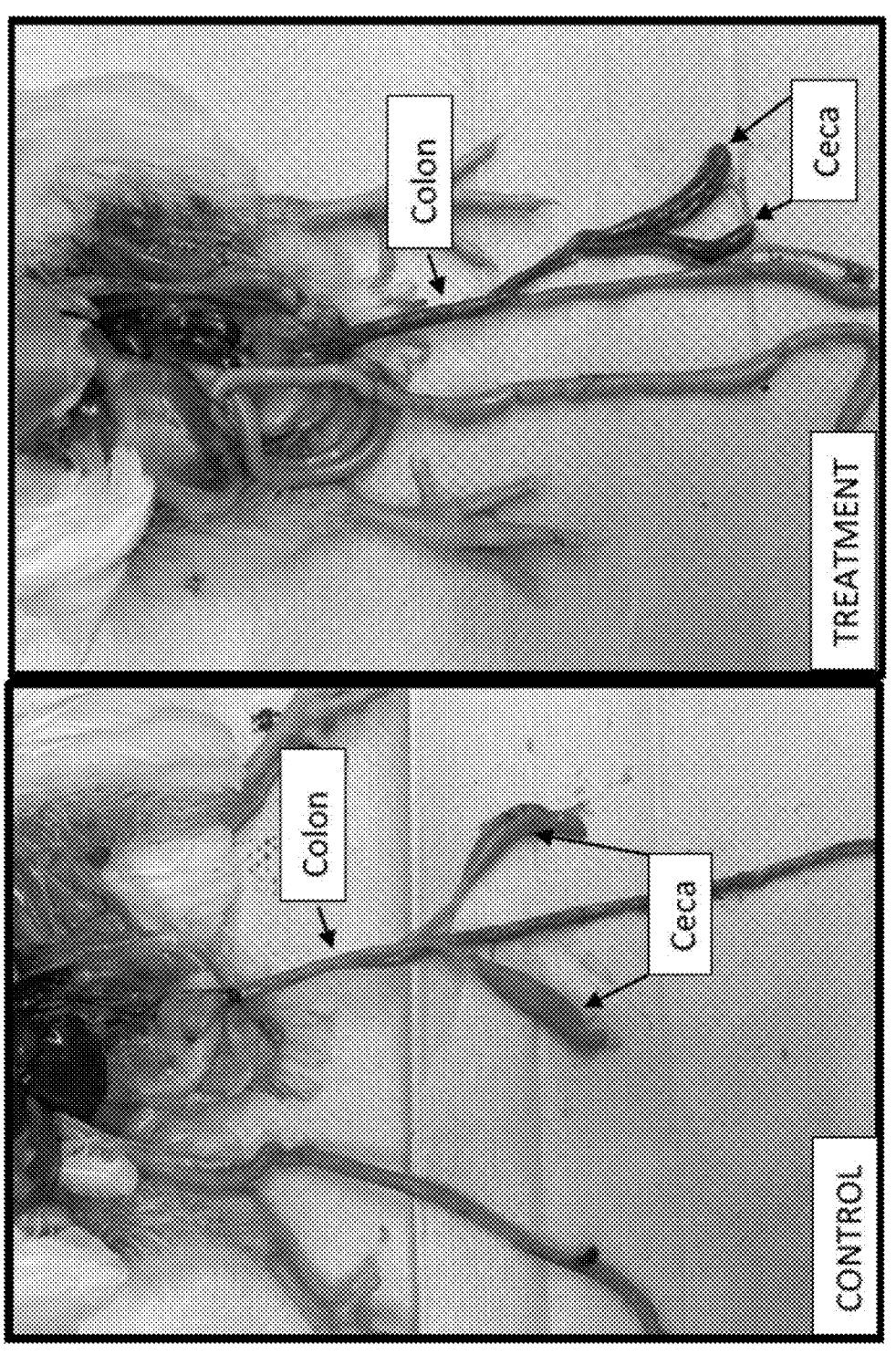
FIGS. 7A and 7B are color photographs showing the dye reaching the large intestine (ceca and colon) as indicated by the dye (black colored) distribution, as described in EXAMPLE 7 below.

After about 10 min, the birds were opened (necropsy) and the pictures in FIGS. 7A (control) and 7B (experimental) show the dye reaching the large intestine (ceca and colon) as indicated by the dye (black colored) distribution.

Experiment 2: Administering *Clostridium perfringens* Via Cloacal Route

Two-week-old broiler chickens (n=3) were administered with *C. perfringens* bacteria while the control birds (n=3) received just the culture medium (fluid thioglycollate). The cloacal administration was performed as described above.

Bacterial cultures were used to inoculate chickens. The *C. perfringens* bacteria were grown in a suitable bacterial culture medium (by way of example, fluid thioglycollate medium) overnight for about 15-16 h and were counted. Then, a volume of 0.5 mL containing $5.2\times10^9$ colony forming units (cfu) bacteria were administered intra-cloacally. The results were as presented in Table 2 below:

TABLE 2

| | Treatment | Recovered after 16 h |
|---|---|---|
| Group 1 | *C. perfringens* administered at $5.2 \times 10^9$ | Ave recovery: $1.7 \times 10^9$ |
| Group 2 | Medium-only control | Not detected |

The results of this EXAMPLE show that biological agents such as clostridia can be administered via intra-cloacal route such that these bacteria can reach the large intestinal parts for their colonization. Additional studies evaluate *C. perfringens* colonization at 24, 28 and 72 h post-cloacal inoculation.

Experiment 3: In a separate trial, an intra-cloacal route was used for inoculating broiler chickens with virulent isolates of *C. perfringens* in order to reproduce necrotic enteritis (NE) disease. The available results, based on the lesions developed in the intestine, indicate that cloacally delivered bacteria were able to cause mild NE infection in the inoculated chickens.

Each bird in this trial was inoculated with bacteria in the range of $5\times10^8$-$5\times10^9$ cfu. These numbers differ depending on the study and duration of administration. In this trial it was desired to infect birds with these bacteria to induce an enteric disease.

This EXAMPLE also supports using an intra-cloacal route to administer to administer probiotics and vaccines to evaluate induction of immunity against important enteric pathogens, including pathogenic clostridial bacteria and coccidian parasites. If it is planned to administer probiotics, a representative range for a treatment effective amount comprises about $1\times10^5$ to about $8\times10^9$ cfu, including about $1\times10^5$, $1\times10^6$, $1\times10^7$, $1\times10^8$, or $1\times10^9$ to about $8\times10^9$ cfu depending on the frequency of administration. In some embodiments, the probiotics that can colonize the intestines effectively can involve either single or two administrations; if the probiotics have poor colonizing ability, the frequency of administration can be increased to multiple (3-5) administrations given either daily or in weekly intervals. If it is desired to provide a bacterial vector-based vaccine, a representative amount starts at $1\times10^8$ cfu for a certain period of time, such as but not limited to ranging over about 1 to about 7 days post hatch, including about 2, 3, 4, 5, 6 days post hatch. This time period can include single administration at day of hatch or administered at multiple time points during bird's life to achieve desired effect. For bacterial vectors with efficient gut colonization ability, $1\times10^8$ cfu may provide an effective dosage, while for other vectors with poor to moderate colonization ability, higher cfu dose may be employed. A representative formulation for a probiotic or vaccine can comprises an active agent and a protective biological to deliver the active ingredient, about 0.25 to about 3 centimeters (cm) into the cloaca. In some embodiments, the bioactive active composition can comprise a liposome (see Sercombe et al., *Front. Pharmacol.*, 1 Dec. 2015, pp. 1-13; see also U.S. Pat. Nos. 10,456,459; 7,037,501, each of which are herein incorporated by reference in its entirety), a carbon nanotube (see Zare et al., 2021, International Journal of Nanomedicine 2021:16 1681-1706; U.S. Pat. No. 10,022,435, herein incorporated by reference its entirety), and/or any other protective biological vehicle as would be apparent to one of ordinary skill in the art upon a review of the instant disclosure. See also Renu and Renukaradhya, *Front Bioeng Biotechnol.* 2020 Nov. 13; 8:558349; Muir et al., *Dev Comp Immunol.* March-April 2000; 24(2-3):325-42; and Jin et al, *Int J Pharm.* 2019 Dec. 15; 572; see also U.S. Pat. No. 9,878,036, herein incorporated by reference its entirety. In some embodiments, a vaccine containing a bacterial culture as described above can be used at the research level. In some embodiments, a probiotic or vaccine can be administered in encapsulating bacteria in a suitable biomolecule (for example, nanoparticles and/or liposomes, and the like) to enhance the delivery of these bacteria in the gut compartments. Again, a representative range for bacterial vaccine purposes comprises a range of $1\times10^8$-$5\times10^9$ cfu of bacteria.

In some embodiments, the presently disclosed subject matter provides a probiotic developed for a particular disease for delivery through the vent as a combination product-probiotic plus vaccine. In some embodiments, the probiotic expresses an antigen of interest that would mount immunological protection against a pathogenic agent (see da Silva et al., 2014, *Braz. J. Microbiol.* 45 (4) •December 2014 and Yurina, 2018, *Med. Sci.* 2018, 6(2), 27). In some embodiments, the presently disclosed subject matter provides a probiotic developed for a particular disease for delivery through the vent as a disease prevention product or administered in combination with a commercially available mucosal vaccine product, such as the Infectious Bronchitis virus, *Salmonella* or Coccidiosis vaccines (Wilson et al., 2020, *Mucosal Vaccines* 2020: 811-829). In some embodiments, the recombinant probiotic isolate expressing heterologous antigen(s) of interest that can target a specific disease control. Representative mucosal formulation approaches are disclosed in U.S. Pat. No. 10,258,688, herein incorporated by reference in its entirety. Other representative probiotic and/or vaccine preparation and formulation techniques are described in U.S. Pat. Nos. 10,624,366; 10,022,435; 9,884,099; 9,580,718; 9,393,275; 8,465,755; and 8,431,138, each of which are herein incorporated by reference in its entirety.

While the compositions, systems, and methods have been described herein in reference to specific components, aspects, features, and illustrative embodiments, it will be appreciated that the utility of the subject matter is not thus limited, but rather extends to and encompasses numerous other variations, modifications and alternative embodiments, as will suggest themselves to those of ordinary skill in the field of the present subject matter, based on the disclosure herein. Various combinations and sub-combinations of the components, structures, and features described herein are contemplated and will be apparent to a skilled person having knowledge of this disclosure. Any of the various features and elements as disclosed herein can be combined with one or more other disclosed features and elements unless indicated to the contrary herein. Correspondingly, the subject matter as hereinafter claimed is intended to be broadly construed and interpreted, as including all such variations, modifications and alternative embodiments, within its scope and including equivalents of the claims.

What is claimed is:

1. A method of delivering a bioactive composition to ceca of a bird, the method comprising:
 (a) providing a bioactive composition;
 (b) delivering a treatment effective amount of the bioactive composition to a cloaca of the bird; and
 (c) providing stimulation to a vent of the bird; whereby delivery of the bioactive composition to the ceca of the bird is accomplished, wherein the bioactive composition contains from about one half to about one hundred calories.

2. The method of claim 1, wherein the bioactive composition is water or comprises a water-based solution or suspension.

3. The method of claim 1, wherein the bioactive composition comprises a component selected from the group comprising a prebiotic, a probiotic, a nutrient, an enteric modulator, an osmolyte, a vaccine, fiber, water, and any combination thereof.

4. A method of delivering a bioactive composition to ceca of a bird, the method comprising:
 (a) providing a bioactive composition;
 (b) delivering a treatment effective amount of the bioactive composition to a cloaca of the bird; and
 (c) providing stimulation to a vent of the bird; whereby delivery of the bioactive composition to the ceca of the bird is accomplished, wherein the bioactive composition has an osmotic pressure not greater than 800 milliosmoles.

5. A method of delivering a bioactive composition to ceca of a bird, the method comprising:
 (a) providing a bioactive composition;
 (b) delivering a treatment effective amount of the bioactive composition to a cloaca of the bird; and
 (c) providing stimulation to a vent of the bird; whereby delivery of the bioactive composition to the ceca of the bird is accomplished, wherein the treatment effective amount ranges from about 0.5 to about 7.5 mL of bioactive composition solution per kg of live weight of subject.

6. A method of delivering a bioactive composition to ceca of a bird, the method comprising:
 (a) providing a bioactive composition;
 (b) delivering a treatment effective amount of the bioactive composition to a cloaca of the bird; and
 (c) providing stimulation to a vent of the bird; whereby delivery of the bioactive composition to the ceca of the bird is accomplished, wherein the treatment effective amount ranges from about 0.01 to about 0.06 mL per gram of live body weight.

7. The method of claim 1, wherein the treatment effective amount comprises bacteria ranging from about $1\times10^5$ colony forming units (cfu) to about $8\times10^9$ cfu.

8. The method of claim 1, wherein the bioactive composition comprises a probiotic component and a vaccine component.

9. The method of claim 1, wherein the bioactive composition comprises two or more components present in a synergistically effective amount.

10. A method of delivering a bioactive composition to ceca of a bird, the method comprising:
 (a) providing a bioactive composition;
 (b) delivering a treatment effective amount of the bioactive composition to a cloaca of the bird; and
 (c) providing stimulation to a vent of the bird; whereby delivery of the bioactive composition to the ceca of the bird is accomplished, wherein delivering a treatment effective amount of the bioactive composition to a cloaca of the bird comprises inserting a delivery device into the cloaca for a distance sufficient to provide delivery of the bioactive composition to the ceca, wherein the distance sufficient to provide for delivery of the bioactive composition to the ceca comprises about 0.25 to about 3 centimeters (cm).

11. The method of claim 10, wherein the delivery device comprises a pipette or other blunt tubular device.

12. The method of claim 1, wherein said bird is selected from the group comprising chickens, turkeys, ducks, geese, quail, pheasant, and ostrich.

13. A method of delivering a bioactive composition to ceca of a bird, the method comprising:
 (a) providing a bioactive composition;
 (b) delivering a treatment effective amount of the bioactive composition to a cloaca of the bird; and
 (c) providing stimulation to a vent of the bird; whereby delivery of the bioactive composition to the ceca of the bird is accomplished, wherein the bird is treated prior to, during, and/or after transport.

14. A method of delivering a bioactive composition to ceca of a bird, the method comprising:
 (a) providing a bioactive composition;
 (b) delivering a treatment effective amount of the bioactive composition to a cloaca of the bird; and
 (c) providing stimulation to a vent of the bird; whereby delivery of the bioactive composition to the ceca of the bird is accomplished, further comprising repeating steps (b) and (c) one or more times.

* * * * *